(12) United States Patent
Han

(10) Patent No.: US 8,692,034 B2
(45) Date of Patent: Apr. 8, 2014

(54) CO-PRODUCTION OF METHANOL AND AMMONIA

(75) Inventor: Pat A. Han, Smørum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 13/806,729

(22) PCT Filed: May 13, 2011

(86) PCT No.: PCT/EP2011/002388
§ 371 (c)(1),
(2), (4) Date: Dec. 21, 2012

(87) PCT Pub. No.: WO2011/160745
PCT Pub. Date: Dec. 29, 2011

(65) Prior Publication Data
US 2013/0095029 A1    Apr. 18, 2013

(30) Foreign Application Priority Data
Jun. 24, 2010   (DK) ................................. 2010 00555

(51) Int. Cl.
*C07C 29/48* (2006.01)
*C01C 1/04* (2006.01)

(52) U.S. Cl.
USPC ........................................ 568/910.5; 423/359

(58) Field of Classification Search
USPC ........................................ 568/910.5; 423/359
See application file for complete search history.

(56) References Cited

U.S. PATENT DOCUMENTS

2008/0182911 A1   7/2008   Batdorf

FOREIGN PATENT DOCUMENTS

| EP | 2 192 082 A1 | 6/2010 |
|---|---|---|
| JP | 2000-63115 A | 2/2000 |

*Primary Examiner* — Sikarl Witherspoon
(74) *Attorney, Agent, or Firm* — Dickstein Shapiro LLP

(57) ABSTRACT

Process for the co-production of methanol and ammonia from a hydrocarbon feed without venting to the atmosphere carbon dioxide captured from the methanol or ammonia synthesis gas and without using expensive air separation units, water gas shift and acid gas wash for removal of carbon.

9 Claims, 1 Drawing Sheet

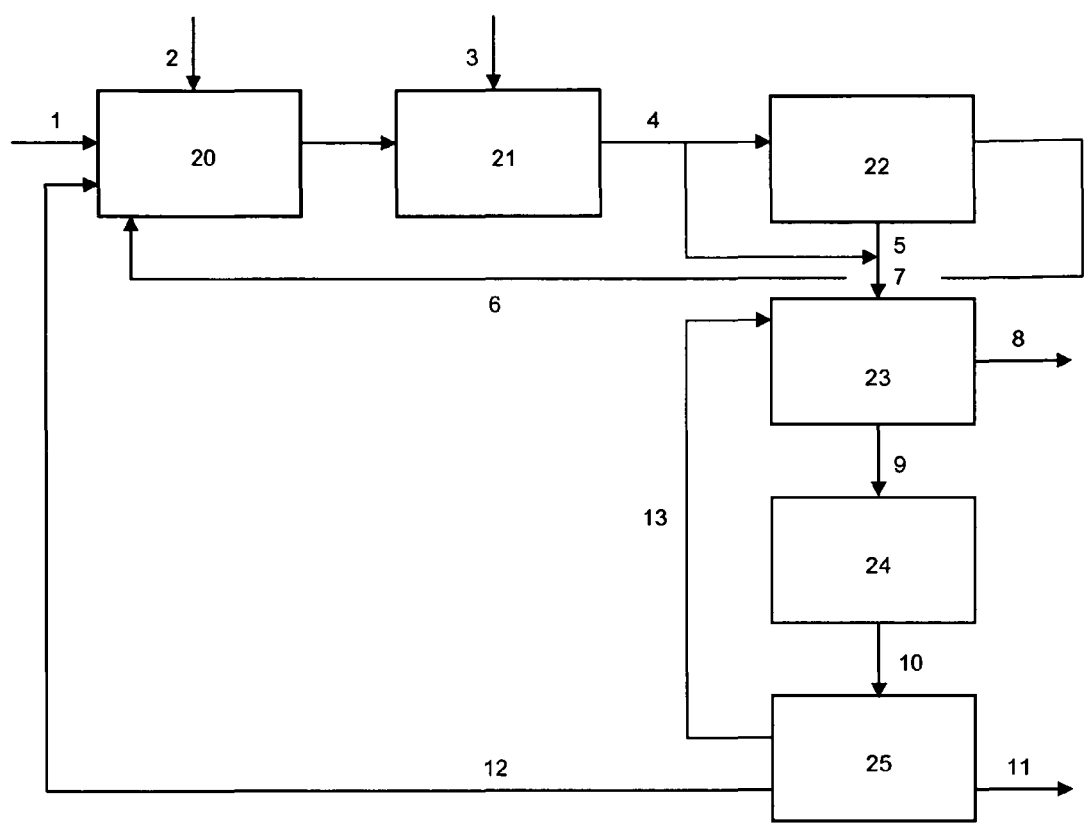

CO-PRODUCTION OF METHANOL AND AMMONIA

The present invention is concerned with a sequential and once-through (single pass) process for the co-production of methanol and ammonia without water gas shift and acid gas wash carbon dioxide removal and without air separation unit used in the reforming section of the plant.

Current processes for co-production of methanol and ammonia involve generally parallel processes in which a common reforming section is used to generate a synthesis gas which is split in separate parallel streams, one of which is used for methanol synthesis and the other for ammonia synthesis. The co-production of methanol and ammonia can also be conducted sequentially or in series, where the synthesis gas produced in the reforming section is first converted to methanol and the unreacted gas containing carbon oxides and hydrogen is subsequently used for ammonia synthesis. Water gas shift and/or carbon dioxide removal steps of the synthesis gas stream are required, thus involving the release of $CO_2$ to the atmosphere and the investment in highly expensive and complicated units for conducting the shift conversion and carbon dioxide removal.

US-A-2007/0299144 discloses in one embodiment a process in which methanol and ammonia are produced in parallel and independently from a common synthesis gas stream and without production of urea. Since urea is not produced there is no need to divert carbon dioxide for urea synthesis. The carbon monoxide in the synthesis gas stream used for ammonia synthesis is converted to carbon dioxide and the reforming is conducted in an oxygen-blown reactor with the oxygen being provided from an Air Separation Unit.

U.S. Pat. No. 6,106,793 describes a process in which methanol and ammonia are produced in parallel and independently. The gas produced in the secondary reforming section is cooled by indirect heat exchange with a gas containing methane and steam in a second primary reforming section to produce an ammonia synthesis gas. The heated gas reacts to produce a methanol synthesis gas comprising CO, $CO_2$ and $H_2$.

EP-A-0,553,631 discloses a process for the production of methanol followed by the production of ammonia. Prior to conducting the ammonia synthesis, unreacted methanol synthesis gas is passed to at $CO_2$-removal step and a nitrogen-wash. An Air Separation Unit provides for the nitrogen in the $N_2$-wash and oxygen for the oxygen-blown secondary reformer upstream the methanol synthesis section.

JP-A-2000063115 describes a process for the co-production of methanol and ammonia. In the reforming section the secondary reformer is air-blown and carbon dioxide is removed from the synthesis gas in order to adjust the syngas composition. There is no need of a shift reactor for converting CO into $CO_2$. The synthesis gas is used for production of methanol in a process which uses recirculation of product stream. Process purged gas from the methanol section is subjected to methanation and then used for ammonia production.

Our EP-A-2192082 describes a process for co-production of methanol and ammonia, where a minimum of flexibility in the product split of methanol and ammonia is promoted; i.e. a minimum of flexibility for control of the product ratio between methanol and ammonia. The product ratio between methanol and ammonia is given by the feedstock composition. This process is simpler and more inexpensive than current processes both in terms of capital costs and operating costs and enables at the same time a minimum release of carbon dioxide to the atmosphere.

It is an object of the present invention to provide a process for co-producing methanol and ammonia as disclosed in EP-A-2192082 but with the option of increasing ammonia capacity without sacrificing the idea of simplicity and inexpensive capital costs and operating costs.

This and other objects are solved by the present invention.

Accordingly, we provide a process for co-producing methanol and ammonia from a hydrocarbon feedstock comprising the sequential steps of:
(a) producing a methanol synthesis gas containing hydrogen, carbon oxides and nitrogen by steam reforming the hydrocarbon feedstock in a primary reforming stage and subsequently in an air-blown secondary reforming stage;
(b) splitting the methanol synthesis gas into a first methanol synthesis gas stream containing 1-50 vol % of the methanol synthesis gas and a second methanol synthesis gas stream containing 50-99 vol % of the methanol synthesis gas, forming a first methanol synthesis gas stream with reduced content of carbon dioxide by passing the first methanol synthesis gas stream through a $CO_2$ Pressure Swing Adsorption ($CO_2$ PSA) while bypassing the second methanol synthesis gas stream, withdrawing an off-gas stream containing hydrogen, carbon dioxide, carbon monoxide and methane from the $CO_2$ Pressure Swing Adsorption, and forming a combined methanol synthesis gas by mixing the first methanol stream with reduced content of carbon dioxide with the by-passed second methanol synthesis stream;
(c) catalytically converting the carbon oxides and hydrogen of the combined methanol synthesis gas in a once-through methanol synthesis stage and withdrawing an effluent containing methanol and a gas effluent containing nitrogen, hydrogen and unconverted carbon oxides;
(d) producing an ammonia synthesis gas without the use of water gas shift and without the use of carbon dioxide removal by removing the unconverted carbon oxides of the gas effluent of step (c) in a catalytic methanation stage and withdrawing an ammonia synthesis gas having a $H_2:N_2$ molar ratio of 3:1;
(e) catalytically converting the nitrogen and hydrogen of the ammonia synthesis gas in an ammonia synthesis stage and withdrawing an effluent containing ammonia and an off-gas stream containing hydrogen, nitrogen and methane.

As used herein the term "carbon oxides" means the components carbon monoxide and carbon dioxide. It would be understood that after the $CO_2$ Pressure Swing Adsorption, most of the carbon dioxide is removed, yet traces of it may still be present in the synthesis gas.

As used herein the term $CO_2$ Pressure Swing Adsorption ($CO_2$ PSA) in step (b) means an arrangement comprising adsorbent material for adsorption of carbon dioxide and in which regeneration of the adsorbent takes place by pressure swing.

It would be understood that in step (b) normally a minor part of the methanol synthesis gas is treated in a $CO_2$ PSA (Pressure Swing Adsorption), while the major part of the synthesis gas is bypassed. Nearly all the carbon dioxide is adsorbed in the $CO_2$ PSA together with minor parts of hydrogen, carbon monoxide and other components. The treated gas, which is rich in hydrogen and carbon monoxide, is mixed with the bypassed synthesis gas. We have found that by introducing a $CO_2$ PSA for treating a minor portion of the methanol synthesis gas, i.e. synthesis make-up gas to the methanol synthesis, it is now possible by simple and relative inexpensive means to increase the ammonia production relative to the methanol production.

As used herein, in the catalytic methanation of step (d) the term "by removing the unconverted carbon oxides" means converting the unconverted carbon oxides to methane. This is evidently different from carbon dioxide removal through the use of absorbers in acid gas washes, which the present invention eliminates.

Accordingly, as used herein the term "carbon dioxide removal" in step (d) means highly expensive $CO_2$-removal stages in the form of acid gas wash, such as conventional MDEA and carbonate wash processes.

As used herein the term "primary reforming stage" means reforming being conducted in a conventional steam methane reformer (SMR), i.e. tubular reformer with the heat required for the endothermic reforming being provided by radiation heat from burners, such as burners arranged along the walls of the tubular reformer.

As used herein the term "air-blown secondary reforming stage" means reforming being conducted in an autothermal reformer or catalytic partial oxidation reactor using air.

As used herein, the term "once-through methanol synthesis stage" means that methanol is produced in at least one catalytic reactor operating in a single pass configuration, i.e. without significant recirculation (not more than 5%, i.e. less than 5%, often 0%) of the volume flow of any gas produced in the methanol synthesis back to the at least one methanol reactor of the methanol synthesis stage, particularly the gas effluent containing hydrogen and unconverted carbon oxides.

Preferably, the hydrocarbon feedstock is natural gas, for instance in the form of liquified natural gas (LNG) or substitute natural gas (SNG).

By the invention we make direct use of the reactions governing reforming, methanol synthesis and ammonia synthesis so that methanol and ammonia can be co-produced without venting carbon dioxide being captured from the synthesis gas. The production of hydrogen by steam reforming is governed by the endothermic reaction $CH_4+H_2O=CO+3H_2$, while methanol synthesis in the absence of carbon dioxide is governed by the reaction $CO+2H_2=CH_3OH$. In the presence of carbon dioxide, methanol is otherwise also generated according to the reaction $CO_2+3H_2=CH_3OH+H_2O$. Ideally the feed synthesis gas for methanol production is a gas containing the highest possible molar ratio $CO/CO_2$. Ammonia synthesis occurs according to the reaction $N_2+3H_2=2NH_3$. Since when conducting the overall process the reforming only produces 3 moles of hydrogen, while methanol synthesis already takes 2 moles of hydrogen and ammonia synthesis requires 3 moles of hydrogen, we restrict on purpose the amount of ammonia to be produced to a third in order to be able to utilize the hydrogen that is available according to $1/3(N_2+3H_2=2NH_3)$. Hence, in a way, by the invention we purposively promote a minimum of flexibility in the product split of methanol and ammonia.

This simple and elegant measure enables the production of about 75-80 wt % methanol and 20-25 wt % ammonia at any time in a process which is simpler and less costly than conventional ones because the process obviates the need to use highly expensive water gas shift stages for the conversion of carbon monoxide into hydrogen and carbon dioxide and also obviates the need to use highly expensive $CO_2$-removal stages, i.e. acid gas wash, such as the conventional MDEA and carbonate wash processes. Operating costs are also kept at minimum since there is no need for shift catalyst replacement and no need for solvent replenishment in the $CO_2$-removal processes. This contrasts other combined processes for the production of methanol and ammonia, such as that of JP 2000063115, where highly expensive removal of carbon dioxide via conventional $CO_2$ stripper or absorber is necessary in order to adjust the $CO_2/CO$ ratio in the synthesis gas and thereby achieve flexibility in the process. In addition, since the secondary reforming is conducted in an air-blown secondary reformer (air-blown autothermal reformer) in order to provide for the required nitrogen there is no need for expensive and massive Air Separation Units (ASU), thereby also making the process less costly than current processes where ASU plants are often required for oxygen supply in autothermal reformers and in which the attendant nitrogen production is normally used in a subsequent nitrogen wash.

The process of the present invention is environmentally friendly because there are no emissions to the surroundings of the $CO_2$ captured from the methanol and ammonia synthesis gas. Practically all carbon monoxide (and carbon dioxide) produced in the process is used for methanol synthesis.

The process is applicable for any plant capacity including large plants producing more than 2000 MTPD ammonia and methanol, for instance 3000, 5000 MTPD or even more.

The methanol synthesis stage is preferably conducted by conventional means by passing the synthesis gas at high pressure and temperatures, such as 60-150 bar, preferably 120 bar and 150-300° C. through at least one methanol reactor containing at least one fixed bed of methanol catalyst. A particularly preferred methanol reactor is a fixed bed reactor cooled by a suitable cooling agent such as boiling water, e.g. boiling water reactor (BWR). In a specific embodiment the methanol synthesis stage in step (c) is conducted by passing the synthesis gas through one boiling water reactor and subsequently through an adiabatic fixed bed reactor, or by passing the synthesis gas through a series of boiling water reactors and subsequently through an adiabatic fixed bed reactor. Preferably, the boiling water reactor is in the form of a single reactor of the condensing-methanol type which comprises within a common shell a fixed bed of methanol catalyst particles and cooling means adapted to indirectly cooling the methanol synthesis gas with a cooling agent, and which preferably operates at pressures above 90 bar and below 150 bar, more preferably above 110 bar and below 130 bar, as described in our patent applications WO-A-09106231 and WO-A-09106232. The use of a methanol reactor according to these applications enables operation at pressures much higher than conventional boiling reactors, which normally are about 80 bar. In addition it enables the use of a single reactor rather than two conventional boiling water reactors, thereby significantly reducing plant costs. Furthermore, since the operating pressure in the methanol synthesis stage can be kept as high as about 120 bar or even higher there are significant savings in terms of equipment size and overall investment costs, as methanol synthesis is favoured at high pressures.

Accordingly, the invention enables the operation of the methanol and ammonia synthesis section at similar operating pressures, for instance 130 bar, which implies a simplified process with significant savings in size of equipment as mentioned above. Yet it is also possible to operate at two different operating pressures, for instance 80 bar in the methanol synthesis stage and 130 bar in the ammonia synthesis stage, which implies energy savings in the methanol synthesis stage.

In step (c) the effluent containing methanol is preferably a liquid effluent. This effluent is obtained by cooling and condensation of the synthesis gas from the methanol reactors. Accordingly, the process of the invention may further comprise cooling the synthesis gas withdrawn from each methanol reactor to condense methanol and passing the gas through a separator, withdrawing a bottom fraction from the separator containing the raw methanol, withdrawing an overhead fraction containing synthesis gas which is passed to the subsequent methanol reactor, and forming a single liquid effluent containing methanol by combining the bottom fractions of the separators of each reactor containing the raw methanol.

It would be understood that the term "methanol reactor" as used herein encompasses adiabatic fixed bed reactors and cooled reactors such as boiling water reactors and reactors of the condensing-methanol type which comprises within a common shell a fixed bed of methanol catalyst particles and cooling means adapted to indirectly cooling the methanol synthesis gas with a cooling agent.

Since the methanol synthesis stage is once-through, there is no need for recirculation of a part of the overhead fraction from the separator of the adiabatic fixed bed reactor back to the first methanol reactor of the methanol synthesis stage. This contrasts other combined processes for the production of methanol and ammonia such as that of JP 2000063115 where methanol synthesis involves significant recirculation of product gas.

In step (d) the catalytic methanation stage for conversion of carbon oxides to methane is conducted in at least one methanation reactor, which is preferably an adiabatic reactor containing a fixed bed of methanation catalyst.

In step (e) the ammonia synthesis gas from the methanation stage containing the right proportion of hydrogen and nitrogen ($H_2:N_2$ molar ratio of 3:1) is optionally passed through a compressor to obtain the required ammonia synthesis pressure, such as 120 to 200 bar, preferably about 130 bar. Ammonia is then produced in a conventional manner by means of an ammonia synthesis loop comprising at least one ammonia converter containing at least one fixed bed of ammonia catalyst, with interbed cooling. The effluent containing ammonia contains also hydrogen, nitrogen and inerts such as methane and argon. Ammonia may be recovered from the effluent containing ammonia as liquid ammonia by condensation and subsequent separation. Preferably, an off-gas stream containing hydrogen, nitrogen and methane is withdrawn from the ammonia synthesis stage, as also is a hydrogen-rich stream (>90 vol % $H_2$). These streams may for instance stem from a purge gas recovery unit. Preferably, this hydrogen stream is added to the methanol synthesis stage (step (c)), for instance by combining with the methanol synthesis gas. The recycle of this hydrogen-rich stream enables a higher efficiency in the process as useful hydrogen is utilised in the methanol synthesis and subsequent ammonia synthesis rather than simply being used as fuel.

In order to improve the energy efficiency of the process the off-gas stream containing hydrogen, nitrogen and methane of step (d) is returned to step (a), i.e. it is returned as off-gas fuel to the reforming section of the plant, specifically to the primary reforming stage. Preferably, also the off gas from the $CO_2$ PSA in step (b), which contains hydrogen, carbon dioxide, carbon monoxide and methane, is used as fuel for the primary reforming stage.

By adsorption of $CO_2$, the ratio of CO and CO2 can be changed to be more favorable for the methanol synthesis and thereby a lower slip of unconverted carbon oxides, mainly carbon dioxide, can be obtained from the methanol synthesis. Carbon monoxide is easy to convert to methanol whereas carbon dioxide is much more difficult to convert. With a lower slip of carbon oxides, less hydrogen is required in the conversion of carbon oxides into methane and thus more hydrogen is available for ammonia production and less methane is created. Less methane in the ammonia synthesis make up gas results in lower purging from the ammonia synthesis loop and thereby lower hydrogen loss with the purge gas and more ammonia can be produced.

The $CO_2$ PSA is a relatively inexpensive unit considering both investment and operating costs for removing $CO_2$ compared to a $CO_2$ removal stages in the form of acid gas wash and thereby enable more flexibility in the process. This is different to JP 2000063115 disclosing the obvious options for elimination of carbon dioxide, where highly expensive removal of carbon dioxide via conventional $CO_2$ stripper or absorber is necessary in order to adjust the $CO_2$/CO ratio in the synthesis gas and thereby achieve flexibility in the process. Normally, acid gas wash plants are used to remove $CO_2$ because they simply have a higher efficiency in $CO_2$ removal with no production of off-gases containing valuable H2 and CO for use in downstream methanol and ammonia synthesis processes. By means of the use of $CO_2$ PSA according to the present invention, we purposively accept having a lower efficiency in $CO_2$ removal prior to methanol synthesis and producing off-gas rich in hydrogen and carbon monoxide that cannot directly be used in downstream methanol and ammonia synthesis processes. We have found that $CO_2$ PSA, although not suitable for use in conventional processes for methanol and ammonia synthesis, or conventional processes for co-production of methanol and ammonia, is perfectly suitable for the present application where the plant flexibility with respect to the co-production process of EP-A-2192082 requires to be slightly changed in order to increase the amount of ammonia produced and thereby slightly change the product split of methanol and ammonia. Whereas acid gas washes on potassium carbonate basis do not tolerate high amounts of CO in the gas to be treated (must be normally well below 15 vol % CO) and acid gas washes on amine basis, such as MDEA, do tolerate high content of CO but due to loss of absorption capacity of the amine solution an oversizing must be made to meet the required capacity, the present process with $CO_2$ PSA is perfectly suitable for the treatment of such gases having such high amounts of CO.

The split stream to the $CO_2$ PSA is preferably between 1%-50 wt % and more preferably between 5-25 vol %, most preferably 10-20 vol %. Accordingly, in step (b) the minor portion which is passed through the $CO_2$ PSA is 1-50 vol %, preferably 5-25 vol %, most preferably 10-20 vol % of the methanol synthesis gas, while the major portion that bypasses the $CO_2$ PSA is 50-99 vol %, preferably 75-95 vol %, most preferably 80-90 vol % of the methanol synthesis gas.

The features of the invention, in full accordance with the appended claims, are recited below:

1. Process for co-producing methanol and ammonia from a hydrocarbon feedstock comprising the sequential steps of:
(a) producing a methanol synthesis gas containing hydrogen, carbon oxides and nitrogen by steam reforming the hydrocarbon feedstock in a primary reforming stage and subsequently in an air-blown secondary reforming stage;
(b) splitting the methanol synthesis gas into a first methanol synthesis gas stream containing 1-50 vol % of the methanol synthesis gas and a second methanol synthesis gas stream containing 50-99 vol % of the methanol synthesis gas stream, forming a first methanol synthesis gas stream with reduced content of carbon dioxide by passing the first methanol synthesis gas stream through a $CO_2$ Pressure Swing Adsorption ($CO_2$ PSA) while bypassing the second methanol synthesis gas stream, withdrawing an off-gas stream stream containing hydrogen, carbon dioxide, carbon monoxide and methane from the $CO_2$ Pressure Swing Adsorption, and forming a combined methanol synthesis gas by mixing the first methanol stream with reduced content of carbon dioxide with the by-passed second methanol synthesis stream;
(c) catalytically converting the carbon oxides and hydrogen of the combined methanol synthesis gas in a once-through methanol synthesis stage and withdrawing an effluent containing methanol and a gas effluent containing nitrogen, hydrogen and unconverted carbon oxides;

(d) producing an ammonia synthesis gas without the use of water gas shift and without the use of carbon dioxide removal by removing the unconverted carbon oxides of the gas effluent of step (c) in a catalytic methanation stage and withdrawing an ammonia synthesis gas having a $H_2:N_2$ molar ratio of 3:1.

(e) catalytically converting the nitrogen and hydrogen of the ammonia synthesis gas in an ammonia synthesis stage and withdrawing an effluent containing ammonia and an off-gas stream containing hydrogen, nitrogen and methane.

2. Process according to feature 1, wherein the hydrocarbon feedstock is natural gas or substitute natural gas (SNG).

3. Process according to feature 1 or 2, wherein the methanol synthesis stage in step (c) is conducted by passing the synthesis gas through one boiling water reactor and subsequently through an adiabatic fixed bed reactor, or by passing the synthesis gas through a series of boiling water reactors and subsequently through an adiabatic fixed bed reactor.

4. Process according to feature 3, wherein the boiling water reactor is in the form of a single reactor of the condensing-methanol type, which comprises within a common shell a fixed bed of methanol catalyst particles and cooling means adapted to indirectly cooling the methanol synthesis gas with a cooling agent.

5. Process according to feature 3 or 4 further comprising cooling the synthesis gas withdrawn from each methanol reactor to condense methanol and passing the gas through a separator, withdrawing a bottom fraction from the separator containing the raw methanol, withdrawing an overhead fraction containing synthesis gas which is passed to the subsequent methanol reactor, and forming a single liquid effluent containing methanol by combining the bottom fractions of the separators of each reactor containing the raw methanol.

6. Process according to any preceding feature further comprising withdrawing a hydrogen-rich stream from the ammonia synthesis stage and adding this stream to step (c).

7. Process according to any preceding feature, in which the off-gas stream containing hydrogen, nitrogen and methane of step (e) is returned to step (a).

8. Process according to any preceding feature, in which the off-gas stream of step (b) is returned to step (a).

9. Process according to any preceding feature, in which the first methanol synthesis gas stream contains 10-20 vol % of the methanol synthesis gas and a second methanol synthesis gas stream contains 80-90 vol % of the methanol synthesis gas stream.

The accompanying figure shows a simplified block diagram of the process according to a specific embodiment of the invention including reforming, methanol synthesis stage, methanation stage and ammonia synthesis stage.

Natural gas 1 is added to primary reforming stage 20 (steam methane reformer) under addition of steam 2. The partly reformed gas is then further reformed in air-blown secondary reforming stage 21 (autothermal reformer) under addition of air 3. The methanol synthesis gas 4 containing hydrogen, carbon oxides and nitrogen is cooled in waste heat boiler(s) under the production of steam. Prior to compression to the methanol synthesis, a split stream of approximately 10 vol % is treated in a $CO_2$ PSA stage 22 in order to adsorb carbon dioxide. The treated stream 5, which is rich in hydrogen, carbon monoxide and nitrogen, is mixed with the bypassed synthesis gas to form combined stream 7. This combined stream represents a methanol synthesis gas 7 (make up synthesis gas) having now obtained a higher ratio between carbon monoxide and carbon dioxide, thus resulting in a more reactive synthesis gas for the methanol synthesis. The $CO_2$ PSA off-gas stream 6 containing hydrogen, carbon dioxide, carbon monoxide and methane is used as fuel in the reforming stage. The methanol synthesis gas 7 is then compressed to methanol synthesis pressure (not shown). In methanol synthesis stage 23 the methanol synthesis gas 7 is converted in once-through operation (single-pass operation, no recirculation) under the production of a liquid effluent 8 containing methanol and a gas effluent 9 containing nitrogen, hydrogen and unconverted carbon oxides. Approximately 80 wt % of the total plant capacity goes to the production of methanol of effluent 8. Carbon oxide in gas effluent 9 is hydrogenated to methane in methanation stage 24 thereby generating an ammonia synthesis gas 10 having a $H_2:N_2$ molar ratio of 3:1. The ammonia synthesis gas 10 is then passed through ammonia synthesis stage 25 under the production of an effluent 11 containing ammonia and a recycle stream 12 containing hydrogen, methane and nitrogen which is returned in the form of off-gas fuel stream 12 to the primary reforming stage 20. A hydrogen-rich stream 13 (>90 vol % $H_2$) is also withdrawn from the ammonia synthesis stage 25. This stream is added to the methanol synthesis stage 23 by combining with the methanol synthesis stream 7. Approximately 20 wt % of the total plant capacity goes to the production of ammonia in effluent 11. The plant obviates the use of Air Separation Units (ASU) as well as water gas shift and particularly $CO_2$-removal stages in the form of acid gas washes.

The following table shows the temperatures, pressures and flow rates of the different streams for a process according to FIG. 1 where we are able to produce approximately 3000 MTPD methanol and 960 MTPD ammonia. It is shown that by the invention it is now possible to properly remove $CO_2$ prior to methanol synthesis and thereby impart flexibility in the process. With respect to the co-production process of our EP-A-2192082 where 750 MTPD ammonia is produced, flexibility is purposively slightly changed in order to increase the amount of ammonia produced to 960 MTPD. The feedstock used is natural gas (93 vol % methane):

TABLE

| Position | Temp. °C. | Pressure Bar g | Flow rate/kmol/h ||||||| 
|---|---|---|---|---|---|---|---|---|---|
| | | | $H_2O$ | $H_2$ | $N_2$ | $CH_4$ | CO | $CO_2$ | Ar |
| 4 | 934 | 30.1 | 6229 | 13185 | 1748 | 568 | 3324 | 1100 | 19 |
| 5 | 48 | 28.1 | 0 | 1334 | 150 | 34 | 263 | 0 | 2 |
| 6 | 48 | 0.5 | 6 | 116 | 42 | 29 | 102 | 121 | 0 |
| 7 | 43 | 131 | 33 | 14233 | 1741 | 603 | 3172 | 961 | 23 |
| 9 | 44 | 124.4 | 8 | 5400 | 1724 | 587 | 13 | 47 | 23 |
| 10 | 42 | 122.8 | 6 | 5170 | 1724 | 649 | 0 | 0 | 23 |

The invention claimed is:

1. Process for co-producing methanol and ammonia from a hydrocarbon feedstock comprising the sequential steps of:
   (a) producing a methanol synthesis gas containing hydrogen, carbon oxides and nitrogen by steam reforming the hydrocarbon feedstock in a primary reforming stage and subsequently in an air-blown secondary reforming stage;
   (b) splitting the methanol synthesis gas into a first methanol synthesis gas stream containing 1-50 vol % of the methanol synthesis gas and a second methanol synthesis gas stream containing 50-99 vol % of the methanol synthesis gas stream, forming a first methanol synthesis gas stream with reduced content of carbon dioxide by passing the first methanol synthesis gas stream through a $CO_2$ Pressure Swing Adsorption ($CO_2$ PSA) while bypassing the second methanol synthesis gas stream, withdrawing an off-gas stream containing hydrogen, carbon dioxide, carbon monoxide and methane from the $CO_2$ Pressure Swing Adsorption, and forming a combined methanol synthesis gas by mixing the first methanol stream with reduced content of carbon dioxide with the by-passed second methanol synthesis stream;

(c) catalytically converting the carbon oxides and hydrogen of the combined methanol synthesis gas in a once-through methanol synthesis stage and withdrawing an effluent containing methanol and a gas effluent containing nitrogen, hydrogen and unconverted carbon oxides;

(d) producing an ammonia synthesis gas by methanation of unconverted carbon oxides of the gas effluent of step (c) in a catalytic methanation stage and withdrawing an ammonia synthesis gas having a $H_2:N_2$ molar ratio of 3:1 without the use of water gas shift and without further use of carbon dioxide removal;

(e) catalytically converting the nitrogen and hydrogen of the ammonia synthesis gas in an ammonia synthesis stage and withdrawing an effluent containing ammonia and an off-gas stream containing hydrogen, nitrogen and methane.

2. Process according to claim 1, wherein the hydrocarbon feedstock is natural gas or substitute natural gas (SNG).

3. Process according to claim 1, wherein the methanol synthesis stage in step (c) is conducted by passing the synthesis gas through one boiling water reactor and subsequently through an adiabatic fixed bed reactor, or by passing the synthesis gas through a series of boiling water reactors and subsequently through an adiabatic fixed bed reactor.

4. Process according to claim 3, wherein the boiling water reactor is in the form of a single reactor of the condensing-methanol type, which comprises within a common shell a fixed bed of methanol catalyst particles and cooling means adapted to indirectly cooling the methanol synthesis gas with a cooling agent.

5. Process according to claim 3 further comprising cooling the synthesis gas withdrawn from each methanol reactor to condense methanol and passing the gas through a separator, withdrawing a bottom fraction from the separator containing the raw methanol, withdrawing an overhead fraction containing synthesis gas which is passed to the subsequent methanol reactor, and forming a single liquid effluent containing methanol by combining the bottom fractions of the separators of each reactor containing the raw methanol.

6. Process according to claim 1 further comprising withdrawing a hydrogen-rich stream from the ammonia synthesis stage and adding this stream to step (c).

7. Process according to claim 1, in which the off-gas stream containing hydrogen, nitrogen and methane of step (e) is returned to step (a).

8. Process according to claim 1, in which the off-gas stream of step (b) is returned to step (a).

9. Process according to claim 1, in which the first methanol synthesis gas stream contains 10-20 vol % of the methanol synthesis gas and a second methanol synthesis gas stream contains 80-90 vol % of the methanol synthesis gas stream.

* * * * *